United States Patent
Herlitze et al.

(10) Patent No.: US 9,284,363 B2
(45) Date of Patent: Mar. 15, 2016

(54) SYSTEM AND METHOD FOR CONTROLLING G-PROTEIN COUPLED RECEPTOR PATHWAYS

(75) Inventors: Stefan Herlitze, Cleveland Heights, OH (US); Lynn Landmesser, Shaker Heights, OH (US)

(73) Assignee: Case Western Reserve University, Cleveland, OH (US)

( * ) Notice: Subject to any disclaimer, the term of this patent is extended or adjusted under 35 U.S.C. 154(b) by 1475 days.

(21) Appl. No.: 12/375,114

(22) PCT Filed: Jul. 26, 2007

(86) PCT No.: PCT/US2007/074439
§ 371 (c)(1),
(2), (4) Date: Jan. 26, 2009

(87) PCT Pub. No.: WO2008/014382
PCT Pub. Date: Jan. 31, 2008

(65) Prior Publication Data
US 2010/0009444 A1   Jan. 14, 2010

Related U.S. Application Data

(60) Provisional application No. 60/833,378, filed on Jul. 26, 2006.

(51) Int. Cl.
*C12N 5/00*     (2006.01)
*C07K 14/705*   (2006.01)
*G01N 33/567*   (2006.01)

(52) U.S. Cl.
CPC ........... *C07K 14/705* (2013.01); *C07K 2319/00* (2013.01)

(58) Field of Classification Search
None
See application file for complete search history.

(56) References Cited

U.S. PATENT DOCUMENTS

| | | |
|---|---|---|
| 2003/0040080 A1 | 2/2003 | Miesenbock et al. |
| 2005/0186658 A1 | 8/2005 | Gupta et al. |
| 2007/0099263 A1 * | 5/2007 | Milligan et al. ............. 435/69.1 |

OTHER PUBLICATIONS

Kim et al. Light-Driven Activation of beta2-Adrenergic Receptor Signalling by a Chimeric Rhodopsin Containing the beta2-Adrenergic Receptor Cytoplasmic Loops, Feb. 22, 2005, Biochemistry 44(7):2284-2292.*
Jastrzebska et al. Functional Characterization of Rhodopsin Monomers and Dimers in Detergents, Dec. 25, 2004, Journal of Biological Chemistry 279(52):54663-54675.*
Jackson, T., "Structure and Function of G Protein Coupled Receptors",*Pharmac. Ther.* vol. 50, pp. 425-442, 1991.

* cited by examiner

*Primary Examiner* — John Ulm
(74) *Attorney, Agent, or Firm* — Tarolli, Sundheim, Covell & Tummino LLP

(57) ABSTRACT

A light-sensitive G-protein coupled receptor includes a light sensitive extracellular domain and a heterologous intracellular domain capable of modulating an intracellular signaling pathway.

7 Claims, 8 Drawing Sheets

US 9,284,363 B2

SYSTEM AND METHOD FOR CONTROLLING G-PROTEIN COUPLED RECEPTOR PATHWAYS

RELATED APPLICATIONS

This application claims priority from U.S. Provisional Application No. 60/833,378, filed Jul. 26, 2006, the subject matter which is incorporated herein by reference.

GOVERNMENT FUNDING

This invention was made with government support under Grant No. NS047752 awarded by the National Institute of Health. The government has certain rights in the invention.

FIELD OF THE INVENTION

The present invention relates to a light-sensitive G-protein coupled receptor and to a method of controlling G-protein coupled receptor pathways.

BACKGROUND

G-protein coupled receptors (GPCRs) constitute a major class of proteins responsible for transducing a signal within a cell. GPCRs have three structural domains: an amino terminal extracellular domain, a seven transmembrane domain containing seven transmembrane domains, three extracellular loops, and three intracellular loops, and a carboxy terminal intracellular domain. Upon binding of a ligand to an extracellular portion of a GPCR, a signal is transduced within the cell that results in a change in a biological or physiological property of the cell. GPCRs, along with G-proteins and effectors (intracellular enzymes and channels modulated by G-proteins), are the components of a modular signaling system that connects the state of intracellular second messengers to extracellular inputs.

The GPCR protein superfamily can be divided into five families: Family I, receptors typified by rhodopsin and the β-2-adrenergic receptor and currently represented by over 200 unique members (Dohlman et al., Annu. Rev. Biochem. 60:653-638 (1991)); Family II, the parathyroid hormone/calcitonin/secretin receptor family (Juppner et al., Science 254: 1024-1026 (1991); Lin et al., Science 254:1022-1024 (1991)); Family III, the metabotropic glutamate receptor family (Nakanishi, Science 258 597:603 (1992)); Family IV, the cAMP receptor family, important in the chemotaxis and development of *D. discoideum* (Klein et al., Science 241: 1467-1472 (1988)); and Family V, the fungal mating pheromone receptors such as STE2 (Kurjan, Annu. Rev. Biochem. 61:1097-1129 (1992)).

G proteins represent a family of heterotrimeric proteins composed of α, β, and γ subunits, that bind guanine nucleotides. These proteins are usually linked to cell surface receptors, e.g., receptors containing seven transmembrane domains. Following ligand binding to the GPCR, a conformational change is transmitted to the G protein, which causes the α-subunit to exchange a bound GDP molecule for a GTP molecule and to dissociate from the β, γ-subunits. The GTP-bound form of the α-subunit typically functions as an effector-modulating moiety, leading to the production of second messengers, such as cAMP (e.g., by activation of adenyl cyclase), diacylglycerol or inositol phosphates. Greater than 20 different types of α-subunits are known in humans. These subunits associate with a smaller pool of β and γ subunits. Examples of mammalian G proteins include Gi, Go, Gq, Gs and Gt. G proteins are described extensively in Lodish et al., Molecular Cell Biology, (Scientific American Books Inc., New York, N.Y., 1995), the contents of which are incorporated herein by reference. GPCRs, G proteins and G protein-linked effector and second messenger systems have been reviewed in The G-Protein Linked Receptor Fact Book, Watson et al., eds., Academic Press (1994).

SUMMARY OF THE INVENTION

The present invention relates to a light-sensitive G-protein coupled receptor that comprises a light sensitive extracellular domain and a heterologous intracellular domain capable of modulating an intracellular signaling pathway. The G-protein coupled receptor can comprise an opsin with a heterologous intracellular domain. The opsin can be selected from the group consisting of rhodopsin, blue opsin, and red opsin. In one aspect of the invention, the intracellular domain, can be coupled to a G-protein subunit to affect at least one G-protein pathway selected from the group consisting of a Gi pathway, a Gq pathway, and a Gs pathway.

In another aspect of the invention, the intracellular domain can correspond to at least a portion of the 5HT receptor domain effective to modulate serotonergic signaling. The intracellular domain can comprise an amino acid sequence corresponding to an amino acid sequence of at least one 5HT intracellular loop selected from the group consisting of a 5HT-2A loop, a 5HT-1A loop, and a 5HT-4A loop.

The present invention also relates to a mammalian cell that comprises a first light-sensitive G-protein coupled receptor and a second light-sensitive G-protein coupled receptor. The first light-sensitive G-protein coupled receptor can be activated by light having a first wavelength and once activated affect a first cell signaling pathway. The second light-sensitive G-protein coupled receptor can be activated by light having a second wavelength and once activated affect a second signaling pathway. The second wavelength can be different than the first wavelength and the second signaling pathway can be different from the first signaling pathway.

In an aspect of the invention, at least one of the first G-protein coupled receptor and the second G-protein coupled receptor can comprise a light sensitive extracellular domain and a heterologous intracellular domain capable of modulating an intracellular signaling pathway. At least one of the first light-sensitive G-protein coupled receptor and the second G-protein coupled receptor can comprise an opsin with a heterologous intracellular domain. The opsin can be selected from the group consisting of rhodopsin, blue opsin, and red opsin. The intracellular domain can couple a G-protein subunit to affect at least one G-protein pathway selected from the group consisting of a Gi pathway, a Gq pathway, and a Gs pathway. The intracellular domain can correspond to at least a portion of the 5HT receptor domain effective to modulate serotonergic signaling.

The present invention further relates to a method of controlling G-protein coupled receptor pathways in a cell. In the method, a first light-sensitive G-protein coupled receptor and luciferase can be co-expressed in a cell or interconnected cells. An amount of luciferin can then be administered to the cell or interconnected cells. The amount of luciferin administered to the cells can be effective to react with the luciferase and produce light to activate the first G-protein coupled receptor. The first G-protein coupled receptor can be activated by a first wavelength of light and affect a first G-protein signaling pathway.

In an aspect of the invention, a second light-sensitive G-protein coupled receptor can be co-expressed with the first G-protein coupled receptor and the luciferase. The second light-sensitive G-protein coupled receptor can be activated by a second wavelength of light and affect a second G-protein signaling pathway. The second wavelength of light and the second G-protein signaling pathway can be different than the first wavelength of light and the first G-protein signaling pathway.

In a further aspect of the invention, a third light-sensitive G-protein coupled receptor can be co-expressed with the first G-protein coupled receptor and the luciferase, the third light-sensitive G-protein coupled receptor being activated by a third wavelength of light and affect a third G-protein signaling pathway. The third wavelength of light and the third G-protein signaling pathway can be different than the first wavelength of light and the first G-protein signaling pathway.

At least one of the first light-sensitive G-protein coupled receptor, the second light-sensitive G-protein coupled receptor, and the third light sensitive G-protein coupled receptor can comprise an opsin with a heterologous intracellular domain. The opsin can be selected from the group consisting of rhodopsin, blue opsin, and red opsin.

At least one of the first light-sensitive G-protein coupled receptor, the second light-sensitive G-protein coupled receptor, and the third light sensitive G-protein coupled receptor can include an intracellular domain corresponding to at least a portion of the 5HT receptor domain effective to modulate serotonergic signaling.

In yet another aspect of the invention, the first light-sensitive G-protein coupled receptor and the luciferase can be co-expressed in myocardial cells, in spinal cord nerve cells, and brain nerve cells and used to modulate, respectively, contraction of myocardial tissue, motorneuron activity after spinal cord injury, and brain nerve cell activity.

DETAILED DESCRIPTION

Figure 1:
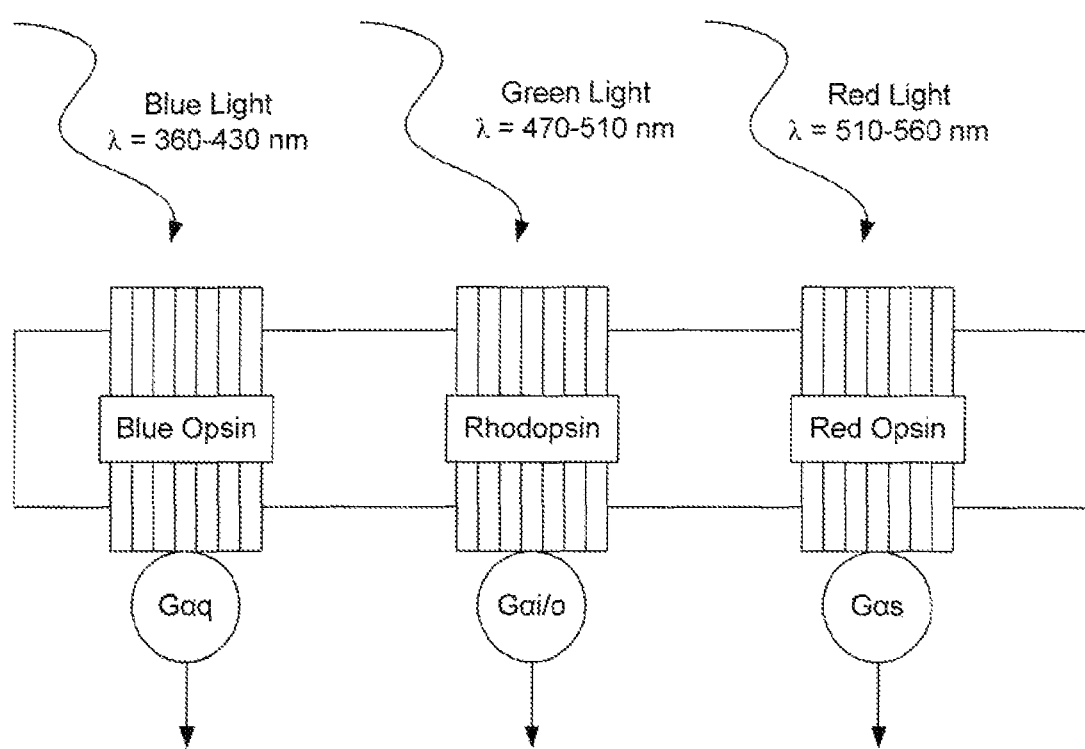
FIG. 1 illustrates the principle of activation of the major GPCR pathways, Gq, Gi/o and Gs by the vertebrate blue opsin (activated by blue light), rhodopsin (activated by green light) and red opsin (activated by red light). GPCR coupling to different G protein pathways is determined by the intracellular protein domains of the GPCR, which will be mutated to allow sufficient coupling of the effector protein.

The present invention relates to light-sensitive (or light-activated) G-protein coupled receptors and to systems and methods of using such GPCRs for controlling GPCR pathways. The light-sensitive GPCRs include a light sensitive extracellular domain and a heterologous intracellular domain capable of modulating an intracellular signaling pathway.

The system and methods of the present invention can allow for simultaneous and/or separated activation of any chosen GPCR pathway and can be applied in any type of cell system. The present invention is based on the idea that the extracellular and transmembrane domains of the vertebrate rhodopsin use light energy to activate G-proteins at the intracellular site of a cell. The intracellular G-protein can be transmitted by the intracellular loops of the GPCR of choice (e.g., 5HT receptor subtypes) and introduced into a light-sensitive GPCR (e.g., rhodopsin/opsin) that can be activated by different wavelengths. The intracellular regions of a GPCR determine the G protein specificity, the precise targeting of the GPCR to subcellular structures, such as dendrites and the interaction with intracellular proteins necessary for subtype and cell type specific function.

In an aspect of the invention, the system and methods of the present invention can be combined with a bioluminescence system, such a luciferase system. Co-expression of luciferase and a GPCR in accordance with the present invention, such as blue-green-red light sensitive GPCRs, in a cell allow for internal activation of GPCR pathways. This is important for performing experiments in living animals (e.g., humans) since the system can be activated by intake or infusion of luciferin in a temporal manner. This system and method can also be used to exploit or determine the role of specific GPCR and in particular the cross-talk of GPCRs in disease as well as be used for drug screens. It will be appreciated that the bioluminescence system need not be limited to a luciferase-luciferin system and that other bioluminescence systems can be used in the invention.

The system and method of the present invention is based on the findings that vetebrate (rat) rhodopsin RO4 can be activated by green light and couples to the Gi/o (pertussin toxin sensitive) pathway in heterologous expression systems as well as neurons and neuronal circuits in chicken embryos. Vertebrate rhodopsin can be activated by light without any addition of ligands, such as all-trans retinal in chicken embryos. Moreover, it was found that light application was sufficient to activate rhodopsin in intact embryos and that light could be applied for several hours indicating that light will penetrate the tissue and will not damage the cells.

Additionally, it was demonstrated that luciferase can activate vertebrate rhodopsin and channel rhodopsin 2 when co-expressed in HEK293 cells. Therefore, the system and methods of the present invention can be used to activate GPCRs or light activated ion channels, such as the green algae channel rhodopsin or light activated enzymes controlling second messenger pathways, in vivo, by injection or intake of the luciferase ligand luciferin, which crosses the blood brain barrier.

Accordingly, the present invention relates to a system for controlling or modulating GPCR pathways. The system can use light to control, for example, the GPCR pathways, Gq (5HT-2A), Gi/o (5HT-1A) and Gs (5HT-4A) within one cell and/or different splice variants within one GPCR family (e.g., 5HT1A, 1B, 1D) in neuronal circuits and animals. The system includes rhodopsins and opsins that are activated by different wavelengths. The intracellular regions of the rhodopsins and the opsins are mutated to allow coupling to the Gi/o, Gs, and Gq pathways. Activation of the respective pathways can be controlled separately or in concert depending on the wavelength applied. Based on the excitation range of opsin/rhodopsins the different receptors can be controlled simultaneously.

In an aspect of the invention, intracellular loops derived from GPCRs involved in serotonergic signaling can be selected to study the effects of light activated intracellular signaling pathways mediated by neurotransmitter serotonin. Malfunctions in the serotonergic transmitter system can cause, for example, schizophrenia, depression, anxiety and obesity and drugs acting via serotonergic GPCRs are used to treat patients for their symptoms.

FIG. 1 illustrates one example of a system in accordance, with an aspect of the invention. The system includes three light-sensitive GPCRs, i.e., blue opsin, rhodopsin, and red opsin, that comprise heterologous intracellular loops. In the system, the intracellular loops of blue opsin are exchanged with 5HT-2A loops for Gq coupling, the intracellular loops of rhodopsin are exchanged with 5HT-1A loops for Gi/o coupling, and the intracellular loops of red opsin are exchanged with 5HT-4A loops for Gs coupling. The system essentially acts a light activated red/green/blue intracellular switch.

G protein specificity of the chimeric light-sensitive GPCRs can be demonstrated in HEK293 cells. Specifically, Gq coupling of the blue opsin/5HT-2A receptor can be demonstrated by monitoring the $Ca^{2+}$ release via activation of phospholipase C/IP3 pathway. Gi/o coupling of the rhodopsin/5HT-1A receptor can be demonstrated by measuring the activation of coexpressed G-protein inward rectifying $K^+$ channels. Gs coupling of the opsin/5HT-4A can be demonstrated by measuring the activation of coexpressed L-type $Ca^{2+}$ channels and AKAP proteins.

In another aspect of the invention Blue-Green-Red switches (e.g., chimeric blue opsin/5HT-2A, rhodopsin/5HT- 1A, red opsin/5HT-4A) can be expressed together with luciferase in the serotonergic transmitter system of transgenic mice using the promoter PET-1. PET-1 allows specific expression of the receptors in serotonergic neurons and the activation of the receptors with luciferin. Expression of these chimeric light-activated (or light sensitive) GPCRs within the brain allows for non-invasive control of neurotransmitter signaling with animals and provides a method to readily determine intracellular phenomenons related to mood changes.

The systems and methods of present invention can also be expressed, for example, in a heart cell via heart specific promoters for modulating the contractions (or excitability) of the heart, in the spinal cord via HB9 promoter for modulating motor neuron activity after spinal cord injury, and in neural cells or brain areas affected by degenerative diseases, such as Parkinson's disease, to control excitability in the brain area a nerve cells of choice.

Example

Fast Noninvasive Activation and Inhibition of Neural and Network Activity by Vertebrate Rhodopsin and Green Algae Channel Rhodopsin A major challenge in understanding the relationship between neural activity and development and between neuronal circuit activity and specific behaviors is to be able to control the activity of large populations of neurons or regions of individual nerve cells simultaneously. Recently, it was demonstrated that neuronal circuits can be manipulated by expressing mutated ion channels or G protein-coupled receptors (GPCRs). The application of these techniques to control neuronal function especially in neural circuits and living animals is limited by their relatively slow time course, the complexity of the constructs to be expressed, or the requirement to apply and wash out ligands. To overcome these limitations, we developed molecular probes that could hyperpolarize or depolarize cells on a ms time scale and be used in intact vertebrate systems to examine behavior. To produce hyperpolarization of the somato-dendritic membrane or inhibition of synaptic transmitter release, the GPCR rat rhodopsin 4 (RO4), a member of the vertebrate rhodopsin family, that acts via the Gi/o pathway to regulate excitability by increasing somato-dendritic $K^+$ and decreasing presynaptic $Ca^{2+}$ conductances in neurons, was used. To depolarize the cell membrane, channel rhodopsin (ChR2) from the green algae *Chlamydomonas reinhardtii*, a cation selective channel directly gated by light, was expressed to produce a high $Na^+$ conductance. The properties of these light-activated switches were extensively characterized and shown to be useful for modulating neuronal excitability and synaptic transmission in cultured-hippocampal neurons. They were then introduced into the embryonic chick spinal cord and shown to be capable of controlling spontaneous rhythmic activity in isolated cords and living embryos.

Materials and Methods

Plasmid Constructs

For constructing ChR2(1-315)-GFP, cDNA of ChR2 (GenBank accession no. AF461397) was PCR-amplified and cloned into HindIII and SacII sites of p EGFP-N1 (Clontech). SinRep(nsP2S$^{736}$)dSP-EGFP was constructed by subcloning another subgenomic promoter with EGFP into the ApaI site of the original SinRep(nsP2S$^{726}$) following the procedure described in *J. Neurosci. Methods* 133, 81-90, which is herein incorporated by reference. RO4 and ChR2(1-315) were cloned into the XbaI and MluI sites of SinRep(nsP2S$^{726}$)dSP-EGFP. Muscarinic AChR M2 (human) was cloned into pcDNA3.1(+) and purchased from the UMR cDNA Resource Center (Rolla, Mo.). Sindbis virus vector SinRep(nsP2S$^{726}$) and helper DH-BB were kindly provided by P. Osten (Max Planck Institute for Medical Research, Heidelberg) and RO4 by A. Huber (University of Karlsruhe, Karlsruhe, Germany) (GenBank accession no. Z46957).

Cell Culture

Culturing, maintaining, and transfection of human embryonic kidney (HEK) 293 cells (tsA201 cells) and low-density and autaptic hippocampal neurons were performed. To detect the distribution of RO4 and ChR2, neurons were transfected by using the calcium phosphate method.

Viral Production and Infection

Sindbis pseudovirions were prepared according to Ivitrogen's directions (Sindbis Expression System).

Viral titer was $\approx 1 \times 10^8$ unit per ml stocked in −80° C. For neuronal infection, viral solution was added to cultured hippocampal neurons on coverslips in 24-well plates. Expression was detected after 10 h and reached maximal expression after 24 h.

Immunocytochemistry and Image Acquisition

Hippocampal neurons (~2-3 weeks in culture) were transfected with RO4 or ChR2-GFP for 24 h, then fixed with 4% paraformaldehyde and permeabilized with 0.2% Triton X-100 in PBS, Anti-opsin (Sigma) and anti-GFP (Molecular Probes) were used to label RO4 and ChR2-GFP. Anti-synaptobrevin-2 (SYSY) was used to colabel neurons with anti-opsin or anti-GFP. Neurons were incubated with primary antibody overnight at 4° C. and after washing they were incubated with Alex 488- and Alex 568-conjugated secondary antibody (Molecular Probes) for 30 min at room temperature. Cells were embedded in Prolong Gold antifade (Molecular Probes). Images were acquired with a Zeiss LSM 410 confocal microscope and analyzed by using VOLOCITY software (Improvision, Lexington, Mass.). Spinal cord whole mounts were stained with the above antibodies as described by Hanson and Landmesser.

Application of Retinal to RO4- or ChR2-Expressing Cells

Bath application of all-trans retinal [100 nM (Sigma)] 2 min before the experiment was sufficient for light activation of both proteins in all preparations tested, i.e., HEK293 cells, cultured hippocampal neurons, and isolated chicken spinal cord. Exogenous application of retinal compounds was not required for light-mediated activation of RO4 and ChR2 in chicken embryos in ovo.

Phototransduction in many systems involves the isomerization of the photosensitive pigment retinal, an aldehyde of vitamin A. Vertebrates and invertebrates use derivatives of 11-cis retinal, whereas bacteria and plants use all-trans isomers as chromophores. Therefore, it was crucial to investigate which retinal compound had to be applied for sufficient activation of the light switches and/or if different tissues or cell types would be able to provide sufficient photosensitive pigments from their own metabolic substrates. We observed that a single bath application lasting 2 min of all-trans retinal or 9-cis retinal [both 100 nM (Sigma)], but not vitamin A, to cultures of HEK293 cells or rat neurons and to isolated embryonic chick spinal cord preparations was sufficient to enable light-driven events during experiments lasting up to 6 h. Whereas retinal was required for light activation of isolated spinal cord preparations after several hours in vitro, freshly isolated cords did not require it. This finding suggested that such compounds might be present in the developing embryo but be washed out during the experiment. Indeed, light was able to elicit movements in embryos in ova without application of retinal. It is, however, possible that not all tissues will have sufficient amounts of retinal-like compounds to enable, light activation, without their exogenous application.

Electrophysiology and Data Analysis

For P/Q-type and GIRK channel recordings in HEK293 cells, $Ca^{2+}$ channel ($\alpha_1 2.1$, $\beta_{1b}$, and $\alpha_{2\delta}$) or GIRK channel (GIRK1/2) subunits and M2 or RO4 were coexpressed in tsA201 cells, and $Ca^{2+}$ channel-mediated $Ba^{2+}$ or GIRK-mediated $K^+$ currents were measured and analyzed as described (3). For ChR2 recording in HEK293 cells, ChR2 (1-315)-GPF was transfected in tsA201 cells. The pipette solution contained 140 mM KCl, 5 mM EGTA, 2 mM $MgCl_2$, and 10 mM Hepes, pH 7.4, and the bath solution contained 140 mM NaCl, 2 mM $MgCl_2$, 1 mM $CaCl_2$, and 10 mM Hepes, pH 7.4.

Cultured hippocampal neurons were recorded on days 10-14 in vitro 12-24 h after Sindbis virus infection. Extracellular recording solution contained 172 mM NaCl, 2.4 mM KCl, 10 mM Hepes, 10 mM glucose, 4 mM $CaCl_2$, and 4 mM $MgCl_2$ (pH 7.3); internal solution contained 145 mM potassium gluconate, 15 mM Hepes, 1 mM potassium-EGTA, 4 mM Na-ATP, and 0.4 mM Na-GTP (pH 7.3). For presynaptic inhibition and paired-pulse facilitation, only areas containing a single neuron forming excitatory synapses (autapses) were used. The effect of light on firing was tested by silencing synaptic activity with 1 µM 6-cyan-7-nitroquinoxaline-2,3-dione (Sigma) and 10 µM bicuculline (Sigma). Cells were perfused with 100 nM all-trans retinal (Sigma) for 2 min before the experiment and then perfused with external solution (see Discussion for rationale). Carb (10 µM) (Sigma), 5 nM PTX (Sigma), and 50 µM baclofen (Sigma) were used in experiments when indicated.

Illumination of patches was achieved with a TILL Photonics (Planegg, Germany) Polychrome II monochromator containing a 75-W xenon short arc lamp with an output of 250-690 nm and 475 nm was used to excite ChR2 or RO4. The light intensity was $1 \times 10^{-6}$ W measured by power meter (Coherent Santa Clara, Calif.), and the light source was controlled by the EPC9. Light and perfusion traces were programmed in PULSE software.

Spinal Cord Preparation and Measurements.

In ovo electroporation, imaging of motor axons, recording of spontaneous bursting episodes in isolated spinal cord preparations, and the quantification of unit activity were as described by Hanson and Landmesser. Statistical significance throughout the experiments was tested with ANOVA by using IGOR software. Standard errors are given as mean+/−SEM.

Results

Vertebrate Rhodopsin can be Used to Inhibit Neuronal Excitability and Synaptic Transmission Vertebrate rhodopsin couples to the G protein transducin, the α-subunit of which belongs to the Gi subfamily, thus raising the possibility that mammalian rhodopsins would couple to other Gi/o family members. In neurons, the pertussis toxin (PTX)-sensitive Gi/o pathway activates G protein inward rectifying potassium channels (GIRKs) and inhibits presynaptic voltage-gated $Ca^{2+}$ channels, GIRK channels are predominantly expressed on dendrites where they can hyperpolarize neurons. Presynaptic $Ca^{2+}$ channels control transmitter release and inhibiting them via Gi/o-coupled receptors inhibits $Ca^{2+}$ influx and transmitter release.

To determine whether vertebrate rhodopsin could be used as a light-activated switch to reduce neuronal excitability postsynaptically and transmitter release presynaptically, RO4 was coexpressed with either GIRK channel subunits 1 and 2 or the P/Q-type Ca2+ channel, consisting of the $_{\alpha 1}2.1$, $\beta_{1b}$, and $_{\alpha 2}\delta$ subunits. The mAChR M2 (mAChR-M2) was also expressed to serve as a positive control for G protein modulation of GIRK and presynaptic Ca2+ 2+ channels via Gi/o-PTX-sensitive GPCRs, because it modulates both GIRK and P/Q-type $Ca^{2+}$ channels in vivo and in heterologous expression systems. We first demonstrated in HEK cells that both of these channels were modulated by light activation of RO4 in a manner very similar to their modulation via mAChR-M2.

Figure 2:
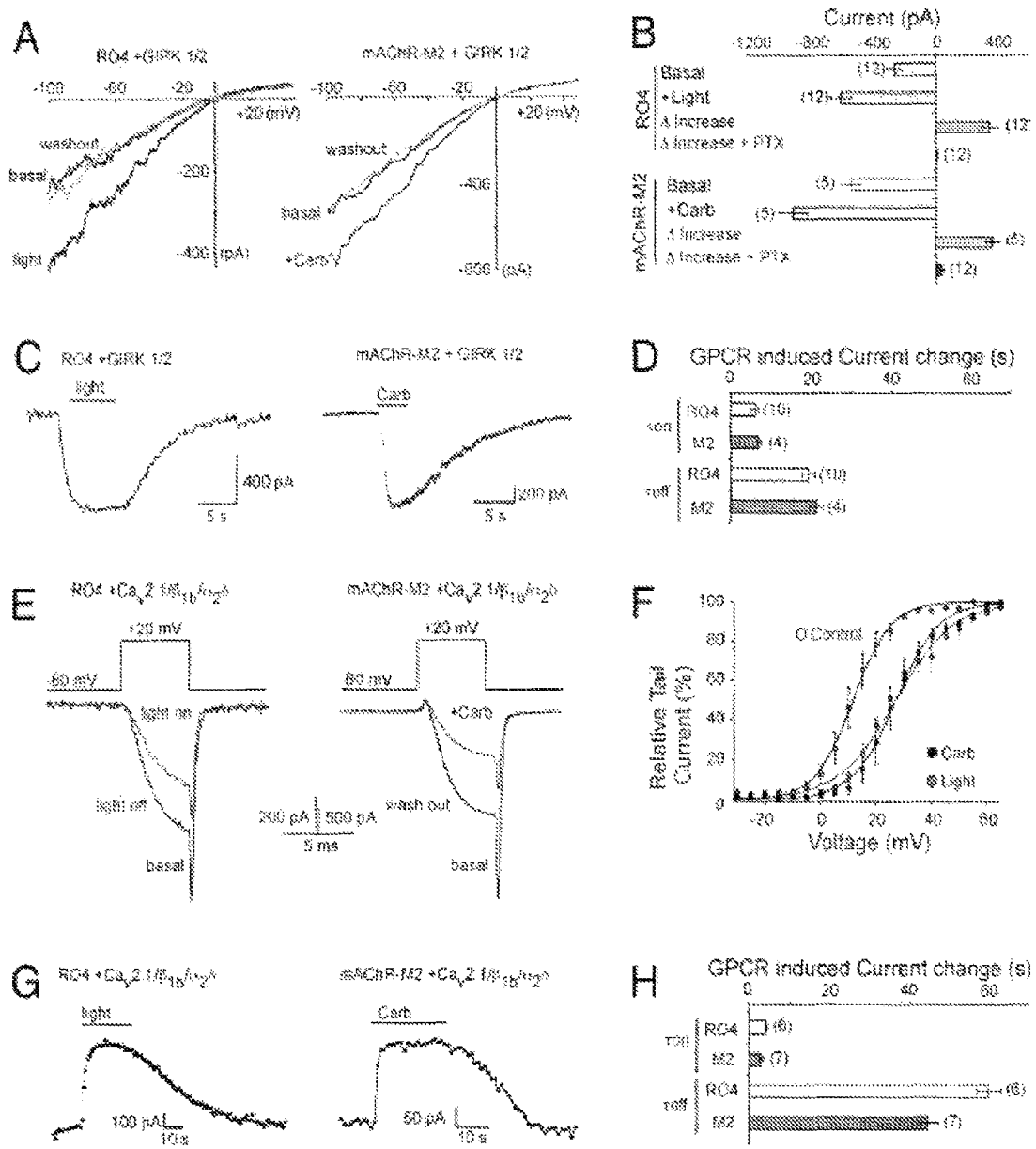
FIG. 2 illustrates plots showing vertebrate rhodopsin modulates GIRK and P/Q-type $Ca^{2+}$ channels via Gi/o-PTX-sensitive pathways. (A) $K^+$ current traces of GIRK1/2 channels coexpressed with RO4 or mAChR-M2 in HEK293 cells before, during, and after light stimulation (Left) or 10 μMCarb application (Right). Currents were elicited by 500-ms voltage ramps from −100 to +50 mV. (B) Comparison of the GPCR-induced current increase in the presence and absence of 5 nmol PTX. (C) Time course traces of GPCR-mediated activation of GIRK currents. GIRK currents were recorded at −60 mV. (D) Comparison of the time constants of the GPCR-induced GIRK current changes before and after GPCR activation. (E) $Ba^{2+}$ current, traces of P/Q-type $Ca^{2+}$ channels ($_{\alpha1}2.1$, $\beta_{1b}$, and $_{\alpha2}\delta$ sub-units) coexpressed with RO4 or mAChR-M2 in HEK293 cells before, during, and after Light stimulation (Left) or 10_MCarb application (Right). (F) GPCR induced depolarizing shift in the voltage dependence of activation curve of P/Q-type $Ca^{2+}$ currents. Currents were elicited from a holding potential of −60 mV by 5-ms-long, 5-mV voltage steps from −10 to +65 mV. Relative tail currents were plotted against the voltage pulses. (G) Time course traces of GPCR-mediated inhibition of P/Q-type $Ca^{2+}$ currents. $Ba^{2+}$ currents were elicited by voltage pulses from −60 to +20 mV and measured every s. (H) Comparison of the time constants of the GPCR-induced P/Q-type channel current changes before and after GPCR activation. Throughout all experiments number in parentheses indicate the number of experiments and statistical significance as indicated (*, $P<0.05$; **, $P<0.01$, ANOVA).
Figure 6:
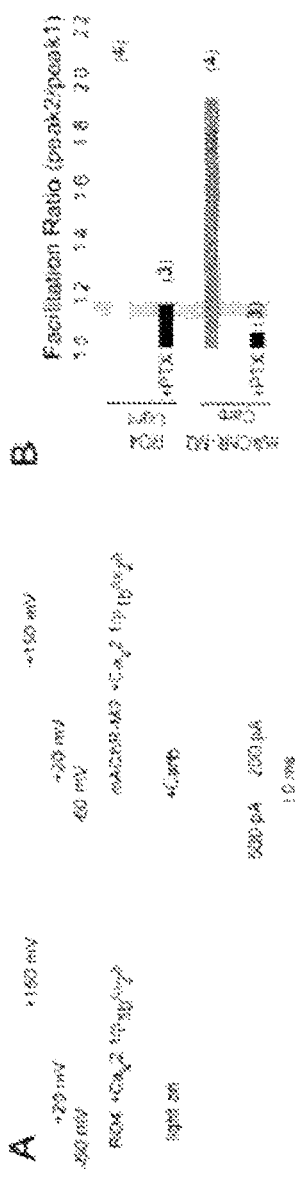
FIG. 6 illustrates activation of vertebrate rhodopsin induces paired-pulse facilitation of P/Q-type $Ca^{2+}$ channels is comparable to the mAChR-M2 induced facilitation. (A) $Ba^{2+}$ current traces of P/Q-type $Ca^{2+}$ channels documenting prepulse facilitation induced by the vertebrate rhodopsin RO4 (Left) or mAChR-M2 (Right) activation. From a holding potential of −60 mV a 5-ms-long first test pulse to +20 mV was elicited. After 1 s a 10-ms-long prepulse to +150 mV was elicited 2 ms before a second 5-ms-long test pulse to +20 mV. The peak current elicited by the second 5-ms test pulse was compared with the peak current elicited by the first 5-ms test pulse and is given as the facilitation ratio (B). (B) Facilitation ratio of P/Q-type $Ca^{2+}$ currents during GPCR activation. Facilitation ratio was determined by dividing the peak current elicited by the second test pulse by the peak current elicited by the first test pulse for the protocol shown in A. In the presence of 50 μM PTX the G protein-mediated inhibition of the $Ca^{2+}$ channel is blocked. Therefore no facilitation is observed.

Activation of the GPCRs by either light or the AChR agonist carbachol (Carb) increased GIRK-mediated $K^+$ currents by comparable amounts (FIGS. 2 A and B) and with comparable activation and deactivation kinetics (FIGS. 2 C and D). Importantly, light activation of RO4 was blocked by prior application of PTX, indicating that activation of GIRK channels by vertebrate rhodopsin is mediated via PTX-sensitive pathways (FIG. 2B). The amount of desensitization during long light or ligand exposure times was modest and comparable between the two [8.7±0.8% (n=4) for mAChR-M2 and 8.7±1.1% (n=4) for RO4], indicating that RO4 can be activated by light over long time periods. When RO4 and mAChR-M2 were coexpressed with the P/Q-type $Ca^{2+}$ channel, light caused reversible inhibition of the $Ca^{2+}$ currents (FIGS. 2 E and G and FIG. 6). Light or Carb caused a similar shift in the voltage dependence of activation to more depolarized potentials (FIG. 2F). In addition, the G protein inhibition caused by light was reversed by high positive prepulses applied shortly before a test pulse (FIG. 6) over a voltage range between −10 and −65 mV (data not shown) similar to the inhibition caused by Carb. Furthermore, light mediated channel inhibition was inhibited by PTX (FIG. 6). The time constants for onset of inhibition and reversal of inhibition were also comparable between RO4 and mAChR-M2 ($\tau_{on}$=3-7 s, $\tau_{off}$≈20-60 s, FIGS. 2 G and H). Thus, vertebrate rhodopsin modulates GIRK and P/Q-type $Ca^{2+}$ channels via PTX-sensitive pathways with similar efficacy and activation and deactivation kinetics as the mAChR.

Figure 3:
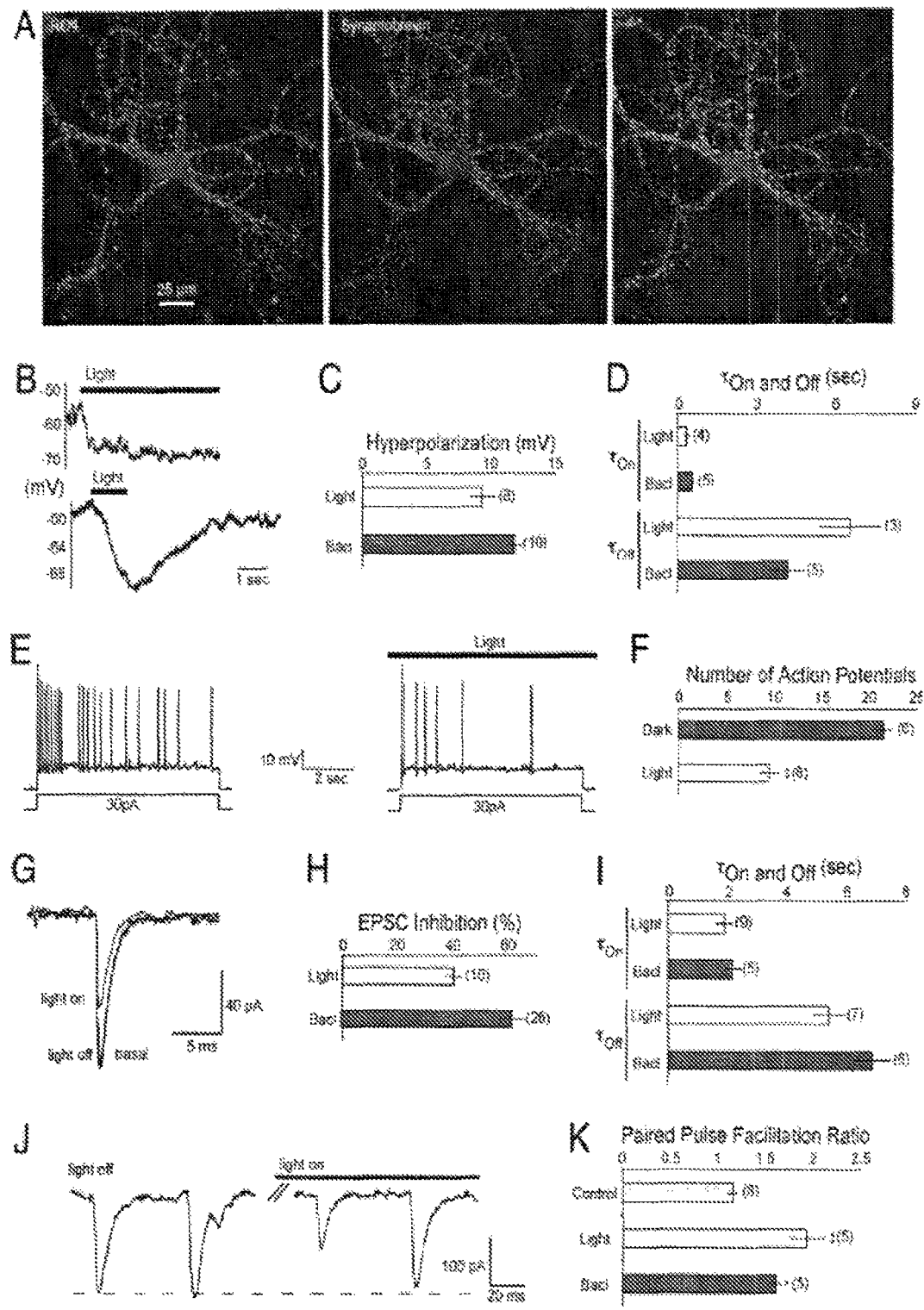
FIG. 3 illustrates functional expression and characterization of vertebrate rhodopsin in cultured hippocampal neurons. (A) Colocalization of RO4 and synaptobrevin in cultured hippocampal neurons. (Left) Fluorescence patterns of neurons from low density hippocampal cultures translated with RO4 reveal a punctate staining. RO4 was detected with an anti-RO4 antibody and visualized with an Alexa 488-coupled secondary antibody. (Center) Hippocampal cells were stained with an antisynaptobrevin II antibody and visualized with an Alexa 568-coupled secondary antibody. (Right) Overlay of RO4 and synaptobrevin II staining. Yellow indicates colocalization. (B) RO4 induced voltage change during a long (Upper) and short (Lower) light pulse. (C) Average GPCR (RO4, GABAB)-induced hyperpolarization of cultured hippocampal neurons. Throughout the experiments GABAB receptors were activated by application of 50 μM baclofen (Bacl). (D) Time course of GPCR (RO4, GABAB)-induced hyperpolarization and recovery from hyperpolarization after switching off the light or washing out baclofen. (E) Voltage traces of current-induced (30 pA) neuronal firing of cultured hippocampal neurons before and during light activation of RO4. (F) Comparison of the number of action potentials measured after current injection for a neuron before and during light activation of RO4. (G) Comparison of EPSC amplitude before, during, and after light application for EPSCs measured in autaptic hippocampal cultures expressing RO4. EPSCs in autaptic hippocampal neurons were elicited by 2-ms voltage pulses from −60 to +10 mV. (H) Comparison of GPCR (RO4, GABAB)-induced EPSC inhibition measured in autaptic hippocampal neurons, (I) Time constants of GPCR (RO4, GABAB)-induced EPSC inhibition and release from inhibition. EPSCs were elicited every 5 s as described in G, (J) Autaptic EPSC traces elicited by 2-ms voltage pulses from −60 to +10 mV separated by 50 ms (20-Hz stimulation) before and after light activation of RO4. (K) Comparison of paired pulse facilitation before and after GPCR (RO4, GABAB) activation for a 20-Hz stimulation protocol. The amplitude of the second EPSC was compared with the first EPSC.

Because RO4 activates GIRKs, which control excitability postsynaptically, and inhibits $Ca^{2+}$ channels, of the $Ca_v 2$ family, which trigger transmitter release presynaptically, we next investigated in cultured hippocampal neurons whether light activation of RO4 could hyperpolarize neurons somato-dendritically to decrease their firing as well as inhibit presynaptic $Ca^{2+}$ influx to modulate short-term synaptic plasticity such as paired-pulse facilitation. Exogenously expressed RO4 was localized somato-dendritically and transported to 70-80% of the synaptic sites where it colocalized with the presynaptic neuronal marker synaptobrevin II (FIG. 3A). Light activation of RO4 induced a 9-mV hyperpolarization within ms comparable to the hyperpolarization induced by activation of endogenous $GABA_B$ receptors by 50 µM baclofen (FIGS. 3 B and C). The hyperpolarization was stable during light application (measured up to 30 s) but was rapidly reversed when the light was switched off (FIGS. 3 B and D). The time constants for hyperpolarization and repolarization were much faster than in HBK293 cells (compare FIGS. 3D and 2C) probably because of the effect of endogenous proteins, such as RGS proteins, which accelerate the GTPase activity of the G proteins. These observations are comparable to the described actions of Gi/o-coupled receptors on membrane changes in neurons. More importantly, the hyperpolarization induced by light was capable of reducing the number of action potentials produced during a depolarizing current pulse (FIGS. 3 E and F).

Because RO4 appeared to be localized at synapses and inhibits P/Q-type $Ca^{2+}$ channels in HEK293 cells, we investigated whether light activation of RO4 could be used to control presynaptic function. We analyzed facilitation properties before and after light application and compared these to the effect of activating the $GABA_B$ receptor with baclofen (FIG. 3 G-K). Light activation of RO4 reduced the excitatory postsynaptic current (EPSC) amplitude by 40% compared with 60% when the GABAB receptor was activated (FIGS. 3 G and H), presumably because of a reduction in quantal content. The time constants for these effects were comparable for both receptors [$\tau_{on}$=0.3-0.6 s, $\tau_{off}$≈4-6 s (FIG. 3I)]. As would be expected if this reduction of EPSC amplitude was caused by a reduction in quanta content, paired-pulse facilitation for both receptor types was increased (FIGS. 3J and K). Taken together, these results show that light activation of RO4 can be used to control cell excitability via hyperpolarization of the somatodendritic membrane as well as presynaptically via reduction of transmitter release.

Figure 7:
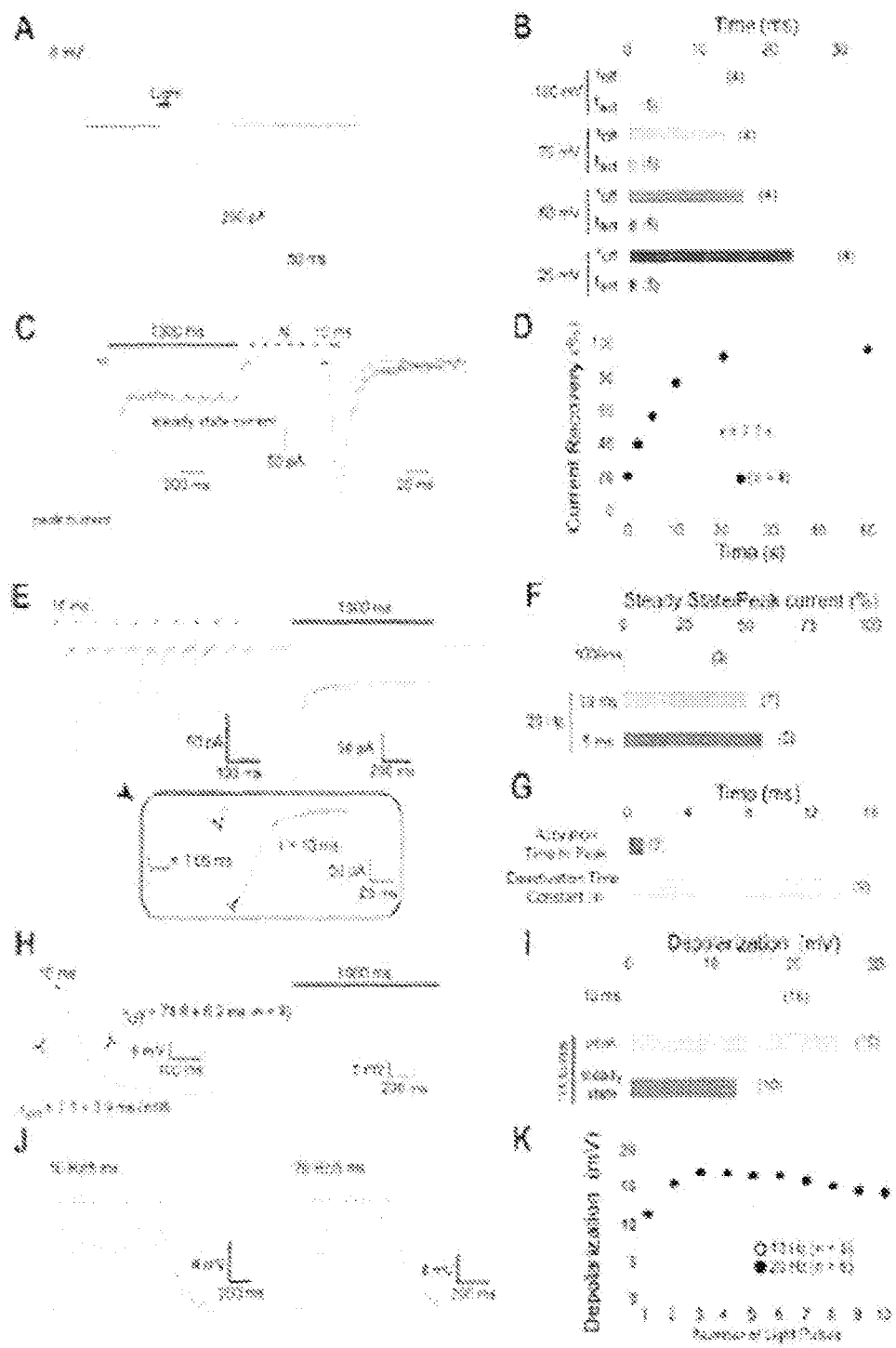
FIG. 7 illustrates biophysical characterization of the C terminally truncated, GFP-tagged ChR2 in HEK293 cells. (A) light-induced ChR2 currents in HEK293 cells after a 10-ms light pulse. Step potentials were from −100 to +50 mV in 25-mV steps. The current traces reveal the inward rectifying behavior of ChR2. (B) Activation and deactivation time constants for ChR2 currents after 10-ms light pulses for the indicated potentials. The deactivation time constant is voltage dependent. The more depolarized the cell the slower is the deactivation of ChR2 currents. (C) Light-induced ChR2 currents measured at −60 mV for the recovery of steady-state current to peak current. (D) Peak current recovery for ChR2 currents after a 1,000-msec light pulse. C and D show that the peak current recovers to 100% of its original value within 20-30 s. (E) Comparison between light-induced ChR2 currents using 10- to 20-Hz/10-ms light pulses in comparison with a continuous 1,000-ms light pulse. (Inset) The second current within the 20-Hz/10-ms light pulse protocol is shown on a larger time scale. The ChR2 activates within a ms. (F) Comparison between light-induced current reduction for ChR2 currents elicited by different light stimulation protocols. E and F illustrate that the shorter the light pulses for ChR2 activation the smaller is the ChR2 current reduction relative to the maximal peak currents. Thus during a prolonged light pulse the ChR2 steady-state current is more reduced than during repetitive, short light stimulation protocols. (G) Activation and deactivation time for ChR2 currents elicited with 10-ms light pulses at −60 mV. (H) Traces of light (ChR2)-induced voltage changes in HEK293 cells after 10-ms (left) or 1,000-ms (Right) light activation of ChR2. (I) Light-induced depolarization mediated by ChR2 for 10- and 1,000-ms light duration. H and I illustrate the time course of the membrane voltage changes during activation and deactivation of ChR2 and demonstrate that the voltage changes are much slower than the underlying current changes. (J) Traces of light (ChR2)-induced voltage changes during a 10- or 20-Hz protocol with 5-ms light pulses. (K) Light-induced depolarization mediated by ChR2 during light trains with different frequencies. J and K illustrate that during repetitive stimulations with frequencies>5 Hz the voltage change mediated by ChR2 current is additive at high-frequency, short-duration light pulses.

Green Algae ChR2 can be Used to Precisely Drive Neuronal Firing on a Fast (ms) Time Scale ChRs are microbial type rhodopsins with an intrinsic light-gated cation conductance. ChR1 from *C. reinhardii* specific for protons, whereas ChR2 is a less selective cation channel with conductance for $H^+>>Na^+>K^+>Ca^{2+}$. Because the conductance of ChR2 is higher than that of ChR1 and the C terminally truncated version of ChR2 (1-315) is as active as the full-length protein, all experiments were carried out with the ChR2 (1-315) fragment fused to GFP at the C-terminal end of ChR2 (1-315). To test whether the ChR2 can act to depolarize cells when activated by light, ChR2 (1-315) was first expressed and extensively characterized in HEK293 cells (FIG. 7). Light activation of ChR2 was found to cause depolarizations of 10-25 mV within 10 ms, with repolarization occurring within 200 ms. Thus ChR2 should be capable of depolarizing neurons sufficiently to elicit action potentials.

Figure 4:
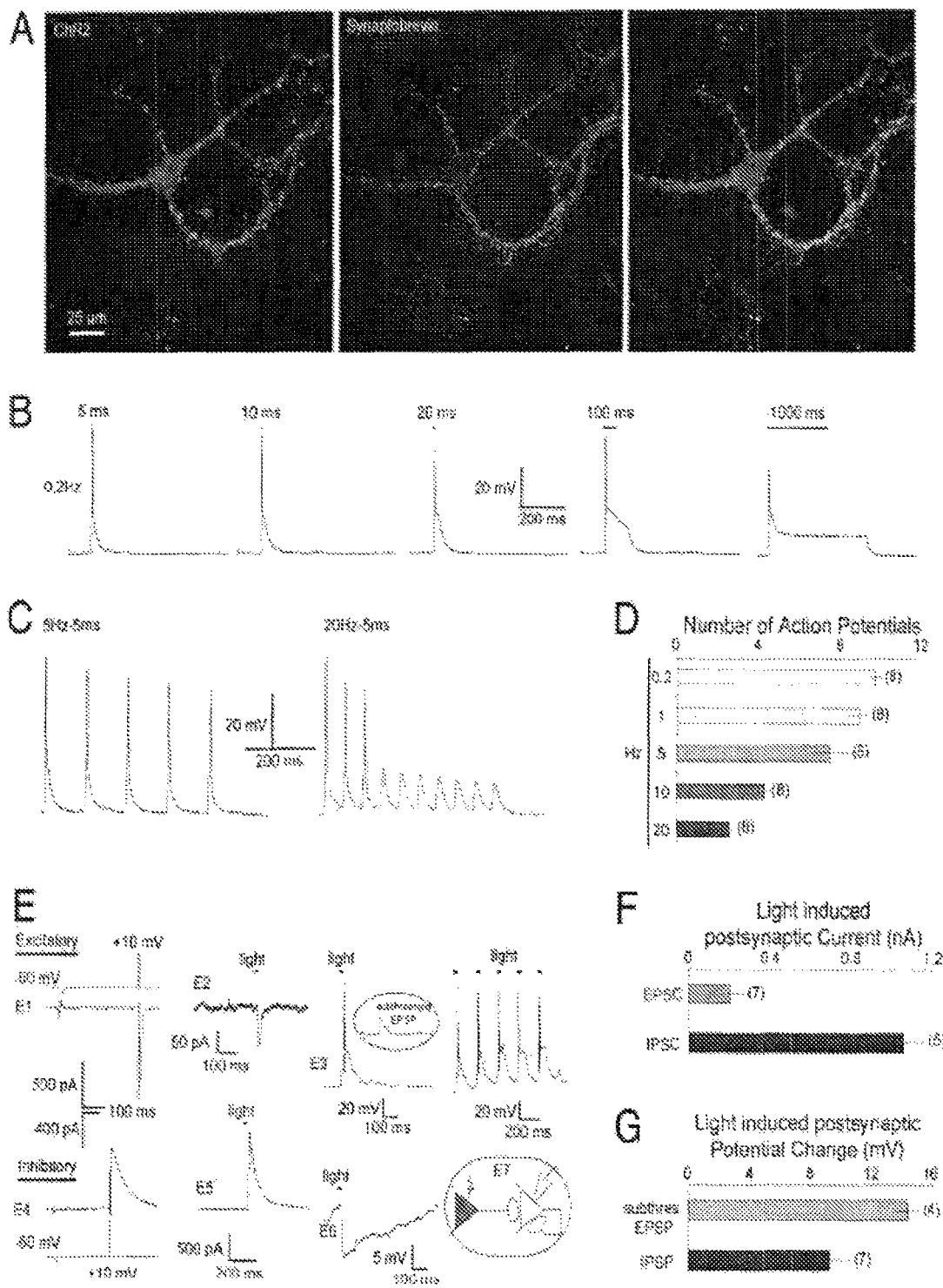
FIG. 4 illustrates functional expression and characterization of green algae ChR2 in cultured hippocampal neurons. (A) Colocalization of ChR2 and synaptobrevin in cultured hippocampal neurons. (Left) Fluorescence patterns of neurons from low-density hippocampal cultures transfected with GFP-ChR2 reveal a punctate staining. (Center) Hippocampal cells were stained with an antisynaptobrevin II antibody and visualized with an Alexa 568-coupled secondary antibody. (Right) Overlay of GFP-ChR2 and synaptobrevin II staining. Yellow indicates colocalization. (B) Voltage traces of ChR2-induced neuronal firing of cultured hippocampal neurons for light stimuli with increasing duration. (C) Voltage traces of ChR2-induced neuronal firing of cultured hippocampal neurons for light stimuli with different frequencies. (D) Number of action potentials measured in neurons expressing ChR2. Action potentials were elicited by a train of 10 stimuli for different light stimulation frequencies with a light duration of 5 ms. (E) Light activation of ChR2 expressed in excitatory (Upper) or inhibitory (Lower) presynaptic neurons induce activation or inhibition in the paired postsynaptic neurons. (E1 and E4) EPSC (Upper) or IPSC (Lower) were elicited by a 2-ms voltage pulse from −60 to +10 mV in the postsynaptic autaptic neuron. (E2 and E5) Light activation of the excitatory and inhibitory presynaptic cells expressing ChR2 induced EPSC (Upper) or IPSC (Lower) on the postsynaptic, autaptic neurons. (E3) Presynaptically (excitatory) light induced spiking or subthreshold depolarization (Inset) of the postsynaptic neuron after a single 5-ms light pulse (Left) or a 10-Hz/5-ms light stimulation protocol (Right). Five light pulses were applied. (E6) Presynaptically (inhibitory) light induced hyperpolarization of the postsynaptic neurons after a single 5-ms light pulse. (E7) Schematic diagram of the neuronal circuit analyzed. Gray indicates the presynaptic neuron expressing ChR2. (F) Average amplitude of the light induced EPSCs or IPSCs. (G) Average amplitude of the light induced hyperpolarization (IPSP) or depolarization (EPSP), when the depolarization was not sufficient to trigger an action potential.

When exogenously expressed in hippocampal neurons, ChR2 appeared to localize both somato-dendritically and at 50-70% of the synaptic sites defined by synaptobrevin 2 immunostaining (FIG. 4A). A 5-ms light activation was sufficient to elicit action potentials in >90% of the experiments performed, whereas longer light exposure led to continuous subthreshold depolarization of the neurons (FIG. 4B). When stimulated at 5 Hz most stimuli elicited action potentials, but as the frequency of stimulation was increased, the proportion that triggered subthreshold EPSPs increased (FIGS. 4 C and D). We next tested whether presynaptically expressed ChR2 was capable of triggering synaptic transmission on postsynaptic neurons. Pairs of hippocampal neurons were analyzed, in which a GFP-ChR2 expressing neuron synapsed with a ChR2-negative neuron that had formed autapses on its own soma (FIG. 4E, $E_7$ diagram). We found that inhibitory postsynaptic currents (IPSCs) as well as EPSCs could be successfully triggered by light activation of the presynaptic neuron (FIG. 4E). The light-activated currents were different in amplitude than the autaptic currents elicited by electrically stimulating the postsynaptic neuron (FIG. 4E), indicating that they are mediated through different neuronal contacts. In three of seven experiments light-activated postsynaptic EPSCs were sufficient to trigger somato-dendritic firing up to 20 Hz. In the remaining four experiments subthreshold EPSPs were observed (FIG. 4E, $E_3$). Light-induced postsynaptic IPSCs caused somatodendritic hyperpolarization (FIG. 4E, $E_6$). As expected the IPSC/EPSC amplitudes and degree of hyperpolarization or depolarization varied between analyzed neuronal pairs, as they would depend on the amount of synaptic contacts formed between the presynaptic and postsynaptic neuron (FIGS. 4 F and G).

Activation of RO4 and ChR2 can be Used to Control Spontaneous Activity in Isolated Intact Spinal Cords and Living Embryos Our next goal was to show that these light-sensitive proteins could be used to control circuit behavior in whole animal preparations. Early embryonic chick spinal cords exhibit rhythmic episodes of spontaneous bursting activity, which are generated by recurrent excitatory connections between motoneurons and GABAergic and glycinergic interneurons, all of which are excitatory at this stage of development. Recently, it has been shown that the normal pattern and frequency of this early spontaneous activity is required for appropriate motor axon path finding in the chick and for the development of cord circuits that enable appropriate flexor extensor and right-left phasing during locomotor-like activity in the mouse.

Figure 5:
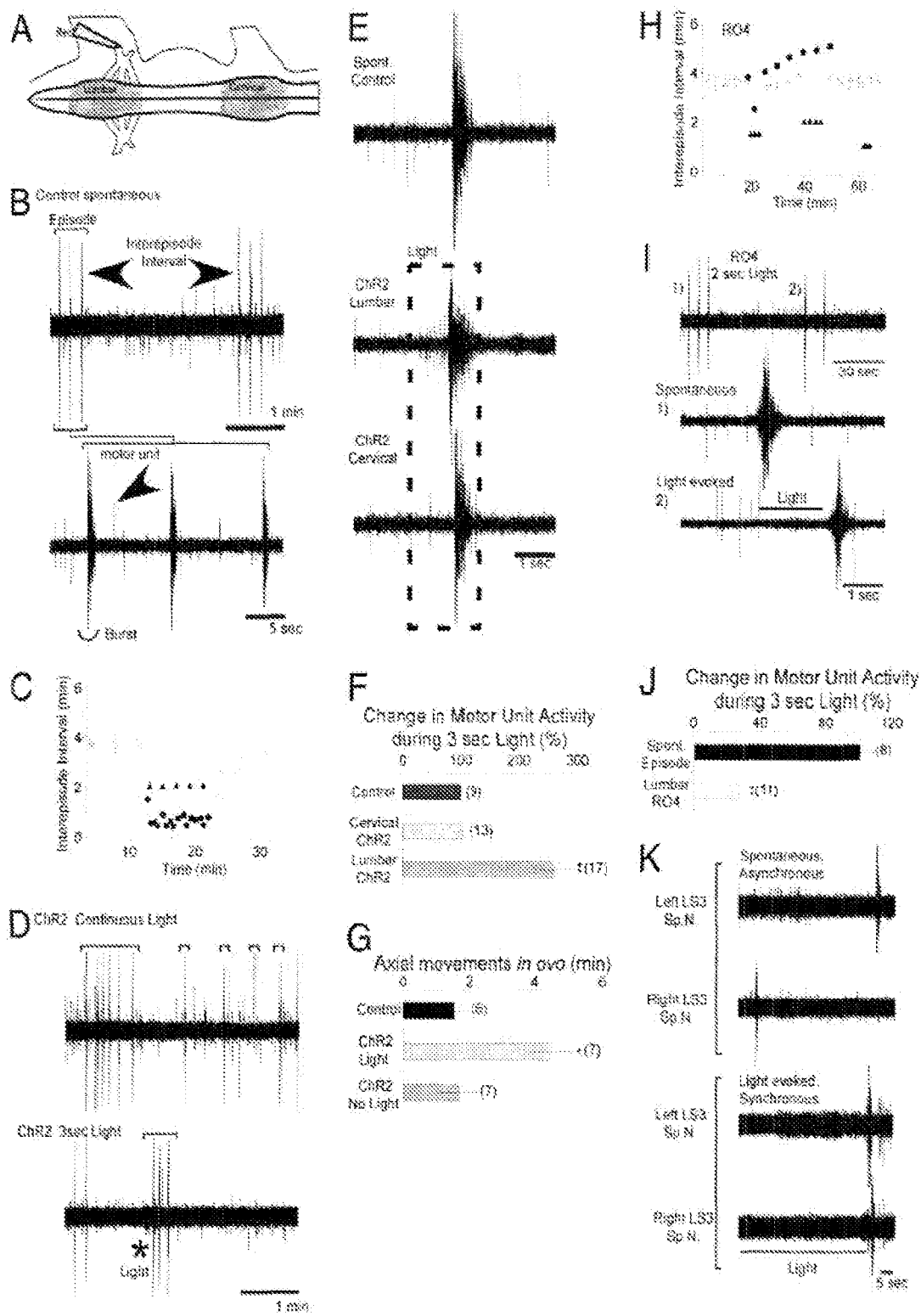
FIG. 5 illustrates RO4 and ChR2 can be used to regulate the frequency of spontaneous rhythmic activity in isolated embryonic chick spinal cords and living embryos. (A) Diagram of isolated chicken spinal cord preparation showing the position of the recording suction electrode; regions electroporated with either ChR2 or RO4 are shown in gray, (B) Electrical recording from motor nerve of ChR2 lumbar-electroporated embryo showing two control episodes in the absence of light (Upper) with an expanded time base trace of a single episode shown (Lower). Bursts of many motor axons firing synchronously and individual motor axons firing asynchronously are noted. (C) Plot of the intervals (in min) between bursting episodes from a lumbar electroporated ChR2 embryo subjected to a long interval of continuous light (circles) or 3-s pulses of light (triangles); filled symbols indicate episodes elicited in the presence of light, and open circles indicate episodes occurring in the absence of light. (D) Electrical recordings showing episodes (denoted by brackets) occurring during several minutes of continuous light (Upper) or elicited by a 3-s pulse of light at the position of the asterisk (Lower). (E) Comparison of unit activity preceding bursts that occurred spontaneously in a nonelectroporated embryo (Top) or were elicited by light when ChR2 was expressed selectively in the lumbar cord (Middle) or cervical cord (Bottom). Time of light exposure is indicated by dashed line. (F) Bar graph of the percent change in motor unit activity occurring in control embryo and one electroporated at cervical or lumbar level during a 3-s exposure to light. (G) The frequency of axial movements of stage 25-26 embryos in ovo, 3 days after ChR2 was electroporated into cervical cord segments, in the presence or absence of 475 nM light. (H) Plot of intervals between bursting episodes in embryos electroporated with RO4 at lumbar level when exposed to a long interval of continuous light (circles) or 3-s light pulses at different repetition rates (triangles); filled symbols indicate episodes occurring in the presence of light, open symbols indicate those that occurred in the absence of light. (I) Activation of RO4 by brief light pulses triggers bursting episodes. (Top) After a spontaneous episode (no. 1) a 2-s light pulse was able to trigger a premature bursting episode (no. 2); both are shown on expanded time bases in Middle and Bottom, respectively (see text for more detail). (J) Bar graph of change in motor unit activity in the period preceding the first burst of a spontaneous episode or one evoked by light activation of RO4. (K) Light activation of RO4 can synchronize the bursting behavior of spinal cord motoneurons. Right and left sides of a RO4 lumbar electroporated cord exhibit independent (asynchronous) rhythms when they are surgically separated at the midline (top pair of traces) However, the bursts triggered after the cessation of a light stimulus results in their synchronization (bottom pair of traces). LS3, lumbar segment 3; Sp.N., spinal nerve.
Figure 8:
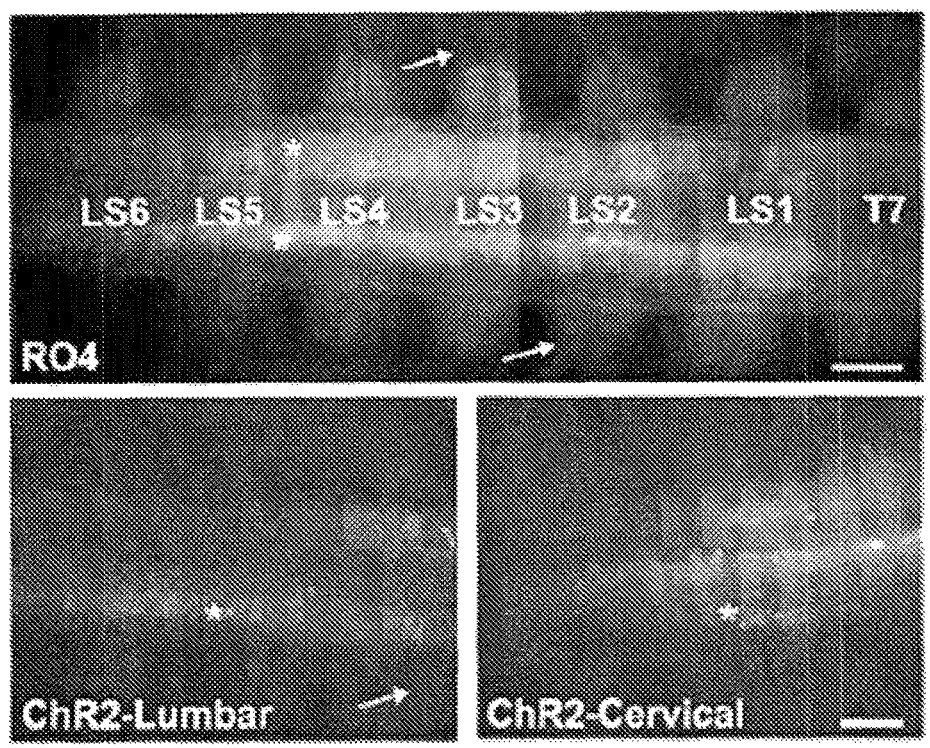
FIG. 8 illustrates expression of RO4 and ChR2 in stage 25-26 (embryonic day 4.5-5) chick spinal cords. Whole-mount spinal cord preparations are viewed from the ventral surface after a ventral laminectomy to allow visualization of cords (caudal, left; rostral, Right). (Upper) In this example, the RO4 construct had been injected into the central canal in the lumbar region of a stage 16 (embryonic day 2.5-3) chicken embryo with the electroporation protocol described by Hanson and Landmesser (1) applied twice, with reversal of electrode polarity in between. This process resulted several days later in extensive expression of RO4 on both sides of the cord from lumbosacral segments (LS) 1-5. There was less strong expression in LS6 and in T (thoracic segment) 7 and no expression at other levels of the cord (data not shown). The extent of expression varied somewhat between embryos and only those with strong expression over most of the lumbosacral cord were chosen for the physiological experiments with RO4. Many motoneurons, identified by their location in the lateral motor column (asterisks) and their axons in the ventral roots, which also contained the construct (arrows), were labeled. The protocol used has been found to also label varying proportions of interneurons, identified by their location in transverse spinal cord sections (G. H., unpublished observations). Based on their locations in cord whole mounts, varying numbers of interneurons were also expressing the electroporated construct in the present experiments, although we did not attempt to quantify their proportion. The extent of the labeling depended on the age of the embryo injected and the amount of construct injected into the central canal. (Lower) ChR2 was electroporated with a similar protocol as above. However, the construct was selectively injected into either the lumbar cord (left), where in this example its expression was higher on the embryo's right side or into the cervical cord (Right), resulting in selective expression in these regions. Asterisks indicate labeling of cells in the lateral motor column and arrows indicate labeled motor axons in the ventral roots. (Scale bar: 100 µm.)

To assess whether such network activity, especially the frequency of spontaneous bursting episodes, could be controlled noninvasively by light, constructs for GFP-ChR2 or GFP-RO4 under the control of the CMV promoter were electroporated into the spinal cords of stage 16 (embryonic day 2-3) chick embryos in ova. At stage 26 (embryonic day 4.5-5) isolated spinal cord-hind limb preparations were made, and the constructs were found to be expressed in many neurons including motor and interneurons (FIG. 8) and could be expressed selectively in lumbar or cervical cord by varying the electroporation protocol. Suction electrode recordings from lumbar motor nerves (FIGS. 5 A and B) revealed that as in control embryos the electroporated embryos exhibited episodes consisting of several bursts every 4 min (FIGS. 5 B and C). Thus the electroporation protocol and expression of these constructs over several days did not appear to have any adverse effects on the development of the cord circuits responsible to generating this activity. The asynchronous firing of individual motoneurons between bursts and between episodes could also be detected (FIG. 5B, arrow). When exposed to continuous light (FIG. 5C, •) the interepisode intervals in this cord, electroporated at the lumbar level with ChR2, were shortened to <1 min. They were, however, less rhythmic than control spontaneous episodes and consisted of single bursts (FIG. 5D Upper). In contrast, the application of a 3-s light pulse was able to elicit a normal three-burst episode shortly after a spontaneous episode (FIG. 4D Lower), and such pulses when repeated could drive episodes at precise frequencies, in the example shown (FIG. 5C, ☆) at 2-min intervals. The expanded time base traces (FIG. 5E) show that light first elicited an increase in lumbar motor unit firing that subsequently resulted in a burst very similar to spontaneous episodes in nonelectroporated embryos. However, when expression of ChR2 was restricted to the cervical cord, lumbar motor nerve recordings revealed that it was also possible to drive episodes in the lumbar cord by light without a previous increase in lumbar unit activity, by generating episodes that propagated from the cervical level (FIGS. 5 E and F). Thus light, as has been previously shown for electrical stimulation, can be used to elicit episodes either by activation of local lumbar interneurons and motoneurons or activation of neurons many cord segments distant.

To assess whether light could be used to drive rhythmic activity in intact embryos in ova, axial movements, which are precisely correlated with electrically recorded episodes of activity, were videotaped under red light that did not activate the cervically electroporated ChR2. When several light pulses of the wavelength necessary to activate ChR2 were given through a window in the shell, each elicited a clear movement episode. Furthermore, a significant increase in the frequency of axial movements could be maintained by continuous application of light over several minutes (FIG. 5G). These observations indicate that the light switches can act in intact animal preparations without application of all-trans retinal (see Discussion) and that the light used is able to penetrate through the amnion and layers of tissue to activate the spinal cord neurons.

Because light activation of RO4 hyperpolarized hippocampal neurons, we next explored whether it could be used to suppress spontaneous bursting activity. During continuous light, the interval between spontaneous episodes increased only modestly in cords with lumbar expression of RO4 (FIG. 5H, •). This finding was not entirely unexpected because regions of cord not electroporated with RO4 would still be able to depolarize and contribute to the excitation required to elicit a bursting episode. Surprisingly, however, a 2-s pulse of light actually elicited a premature episode (5I, 2) 1 min after a spontaneous episode (FIG. 5I, 1). Yet when 1-, 1.5-, or 2-s pulses of light were given, lumbar motor unit activity was suppressed during the light and the episode was triggered only when the light was switched off (FIG. 5I, 2). During the light exposure asynchronous firing of motoneurons was also suppressed (FIGS. 5 I Bottom and J). Thus, while the activation of RO4 in intact cord circuits could affect excitability by the activation of other G protein-coupled pathways, for example, by activating glycine receptors that are excitatory at this stage, our results suggest that in the embryonic day 5 chick cord hyperpolarization of the transfected neurons predominates. We propose that such hyperpolarization of cells within the circuit (27), possibly by relieving the inactivation of voltage-gated $Na^+$ channels, enhances the probability that these cells will fire together, when the light is extinguished and thus provides another means for synchronizing bursting episodes within the circuit. Thus light activation of RO4 could precisely drive episodes at 1-, 1.5-, or 2-s intervals (FIG. 5H, ☆). In addition, when the connections between the right and left sides of the cord are surgically severed, the episodes on the two sides occur asynchronously, but can be synchronized by light activation of RO4 (FIG. 5K).

Discussion

This study has shown that vertebrate rhodopsin RO4 and green algae ChR2 can be used to control neuronal function when activated by light. RO4 acted postsynaptically to hyperpolarize neurons and inhibit action potential firing and presynaptically to reduce transmitter release. We also demonstrated that ChR2 could function somato-dendritically to depolarize neurons and cause action potential firing. Whether it is transported to the presynaptic terminal where currents generated by it could modulate transmission remains to be determined. However, the transport of RO4 to presynaptic sites, where it was capable of modulating presynaptic function (transmitter release and paired-pulse facilitation), suggest that it will be a useful tool for studying G protein-mediated effects at the vertebrate presynaptic terminal in the ms time range and will provide a means for precise temporal activation and deactivation of presynaptic G proteins. Such precise activation is not possible with activating GPCRs with ligands, because washout, transport, or degradation of the ligands is slow. It is likely that ms activation of presynaptic terminal G proteins will lead to insights into the presynaptic function of G proteins, and in particular for events involved in short-term synaptic plasticity and modulation of transmitter release.

ChR2, which appears to be the protein of choice for increasing excitability and firing of neurons, was also very recently characterized, in neuron. We observed that light stimulation frequencies >5 Hz led to a decrease in the success rate of action potential firing, probably because of the use-dependent decrease in ChR2 currents combined with a frequency-dependent increase in $Na^+$ channel inactivation. The 5-Hz stimulation protocol, which we found resulted in a high success rate in eliciting trains of action potentials, is in agreement with the 200-ms time it takes to recover from the ChR2-induced depolarization (FIG. 7). Thus the extent to which a neuron will be able to precisely follow the frequency of light pulses will probably depend on the membrane properties of the different classes of neurons.

A potential concern related to the use of light-activated switches is the extent to which the light will penetrate tissues. However, we demonstrated here that the applied light was sufficient to activate both isolated spinal cords and intact embryonic day 5-6 chick embryos inside the egg, where light was applied through a window in the shell. Furthermore, the fact that light stimuli could be applied to the chick cords over many hours without altering the pattern or frequency of the spontaneous rhythmic activity in the absence of light suggests that the light has not damaged the complex cord circuits required for generating this activity. Taken together, our experiments thus demonstrate that neuronal circuits within intact embryos can be controlled by a noninvasive technique without the need for any chemical compounds.

Thus, the light switches we have developed should provide important tools for characterizing cell and network function in living animals or tissue. Placing these switches under the control of specific promoters will enable one to control the activity of specific subsets of neurons and thus determine their role in complex behaviors, as, for example, defining the roles of subclasses of interneurons and motoneurons in locomotion. Besides their utility for basic characterization of neuronal circuit function and behavior, these proteins will provide additional tools for developing externally, light-controlled molecular machines to circumvent disease or trauma-induced alterations in nervous system excitability, such as after spinal cord injuries, heart arrhythmia, and Parkinson's disease.

All publications cited in this application are herein incorporated by reference in their entirety.

Having described the invention, the following is claimed:

1. A mammalian cell comprising:
   a first light-sensitive G-protein coupled receptor, the first GPCR being activated by light having a first wavelength and once activated affecting a first cell signaling pathway,
   a second light-sensitive G-protein coupled receptor, the second GPCR being activated by light having a second wavelength and once activated affecting a second signaling pathway, the second wavelength being different than the first wavelength and the second signaling pathway being different from the first signaling pathway.

2. The mammalian cell of claim 1, at least one of the first GPCR and the second GPCR comprising a light sensitive extracellular domain and a heterologous intracellular domain capable of modulating an intracellular signaling pathway.

3. The mammalian cell of claim 2, at least one of the first GPCR and the second GPCR comprising an opsin with a heterologous intracellular domain.

4. The mammalian cell of claim 3, the opsin being selected from the group consisting of rhodopsin, blue opsin, and red opsin.

5. The mammalian cell of claim 2, the intracellular domain coupling a G-protein subunit to affect at least one G-protein pathway selected from group of Gi, Gq, and Gs.

6. The mammalian cell of claim 2, the intracellular domain corresponding to at least a portion of a 5HT receptor domain effective to modulate serotonergic signaling.

7. The mammalian cell of claim 1, further comprising luciferase.

* * * * *